United States Patent
Kakinuma et al.

(10) Patent No.: US 10,561,584 B2
(45) Date of Patent: Feb. 18, 2020

(54) DENTAL ADHESIVE AGENT AND METHOD OF MANUFACTURING THEREOF

(71) Applicant: GC Corporation, Shizuoka (JP)

(72) Inventors: Hiroaki Kakinuma, Tokyo (JP); Kensuke Fujimori, Tokyo (JP); Naofumi Matsumoto, Tokyo (JP)

(73) Assignee: GC Corporation, Shizuoka (JP)

( * ) Notice: Subject to any disclaimer, the term of this patent is extended or adjusted under 35 U.S.C. 154(b) by 11 days.

(21) Appl. No.: 15/935,590

(22) Filed: Mar. 26, 2018

(65) Prior Publication Data
US 2018/0280252 A1   Oct. 4, 2018

(30) Foreign Application Priority Data

Mar. 31, 2017   (JP) ................. 2017-069563

(51) Int. Cl.
*A61K 6/083*   (2006.01)
*A61K 6/00*   (2020.01)
*A61K 6/04*   (2006.01)

(52) U.S. Cl.
CPC .......... *A61K 6/0023* (2013.01); *A61K 6/0008* (2013.01); *A61K 6/0091* (2013.01); *A61K 6/04* (2013.01); *A61K 6/083* (2013.01)

(58) Field of Classification Search
CPC .................................. A61K 6/0008
See application file for complete search history.

(56) References Cited

U.S. PATENT DOCUMENTS

| | | | |
|---|---|---|---|
| 2003/0162863 A1* | 8/2003 | Satoh ................. | A61K 6/0052 523/109 |
| 2010/0105802 A1* | 4/2010 | Kuboe ................ | A61K 6/0088 523/116 |
| 2011/0257292 A1* | 10/2011 | Okubayashi ......... | A61K 6/0005 523/115 |
| 2015/0320646 A1* | 11/2015 | Kameya ............... | A61K 6/083 433/90 |
| 2018/0049953 A1* | 2/2018 | Tanaka ................ | A61K 6/08 |

FOREIGN PATENT DOCUMENTS

| | | |
|---|---|---|
| EP | 3272325 | 1/2018 |
| JP | 2013-209598 | 10/2013 |
| WO | 2016/152659 | 9/2016 |

* cited by examiner

*Primary Examiner* — Michael F Pepitone
(74) *Attorney, Agent, or Firm* — IPUSA, PLLC

(57) ABSTRACT

A dental adhesive agent includes a polymerizable monomer; first and second inorganic particles which have been subjected to a surface treatment by a chemical compound, respectively; and a third inorganic particle. The first inorganic particle has a volume median diameter greater than or equal to 0.1 μm and less than or equal to 0.5 μm, the second inorganic particle has a volume median diameter greater than or equal to 0.6 μm and less than or equal to 0.9 μm, and the third inorganic particle has a mean primary-particle diameter greater than or equal to 5 nm and less than or equal to 50 nm. The mass ratio of the third inorganic particle with respect to the gross mass of the first inorganic particle, the second inorganic particle and the third inorganic particle is greater than or equal to 0.001 and less than or equal to 0.05.

11 Claims, No Drawings

DENTAL ADHESIVE AGENT AND METHOD OF MANUFACTURING THEREOF

CROSS-REFERENCE TO RELATED APPLICATION

The present application is based on and claims the benefit of priority of Japanese Priority Application No. 2017-069563 filed on Mar. 31, 2017, the entire contents of which are hereby incorporated by reference.

BACKGROUND OF THE INVENTION

1. Field of the Invention

The present invention relates to a dental adhesive agent and a method of manufacturing the dental adhesive agent.

2. Description of the Related Art

In order to bond a dental prosthesis to a tooth, a dental adhesive agent including a polymerizable monomer, an inorganic particle and a polymerization initiator is used.

As an embodiment of the dental adhesive agent, a two-part adhesive agent (2 pastes) is known that is polymerized and cured by mixing a paste in which an oxidizer, such as peroxide as a chemical polymerization initiator, is included, with a paste in which a reducer, such as tertiary amine as another chemical polymerization initiator, is included (see Patent Document 1, for example).

As another embodiment of the dental adhesive agent, an one-part adhesive agent (1 paste) is known that is polymerized and cured by irradiating light on a paste including a photo polymerization initiator.

Further, a dual-cure dental adhesive agent is also known in which both of a chemical polymerization initiator and a photo polymerization initiator are included.

Recently, dental prostheses manufactured by CAD/CAM have become widespread. However, compared with a case in which dental prostheses are manufactured by conventional methods, such as casting or pressing, the fitting of the dental prostheses manufactured by CAD/CAM may be less accurate. When fixing a dental prosthesis with reduced fitting accuracy to a cheek tooth on which particularly high occlusal pressure is applied, for example, it is required to more strongly bond the dental prosthesis to the tooth, and also a dental adhesive agent with high post-curing bending strength is required.

However, if the amount of the inorganic particle is increased in order to improve bending strength of the dental adhesive agent post-curing, there is a problem that it becomes hard to extrude the dental adhesive agent from a syringe.

Patent Document

[Patent Document 1] Japanese Laid-open Patent Publication No. 2013-209598

SUMMARY OF THE INVENTION

The present invention is made in light of the above problems, and provides a dental adhesive agent whose post-curing bending strength is high and capable of being easily extruded.

According to an embodiment, there is provided a dental adhesive agent, including:
a polymerizable monomer;
a first inorganic particle (A1) that has been subjected to a surface treatment with a chemical compound expressed by a general formula (1),

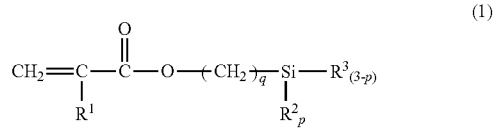

where "$R^1$" is a hydrogen atom or a methyl group, "$R^2$" is a hydrolyzable group, "$R^3$" is a hydrocarbon group whose carbon number is greater than or equal to 1 and less than or equal to 6, "p" is 2 or 3 and "q" is an integer greater than or equal to 6 and less than or equal to 13, having a volume median diameter greater than or equal to 0.1 μm and less than or equal to 0.5 μm;
a second inorganic particle (A2) that has been subjected to a surface treatment with a chemical compound expressed by a general formula (2),

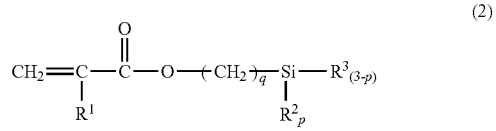

where "$R^1$" is a hydrogen atom or a methyl group, "$R^2$" is a hydrolyzable group, "$R^3$" is a hydrocarbon group whose carbon number is greater than or equal to 1 and less than or equal to 6, "p" is 2 or 3 and "q" is an integer greater than or equal to 6 and less than or equal to 13, having a volume median diameter greater than or equal to 0.6 μm and less than or equal to 0.9 μm; and
a third inorganic particle (B), having a mean primary-particle diameter greater than or equal to 5 nm and less than or equal to 50 nm, wherein a group expressed by a general formula (3) and/or a group expressed by a general formula (4) is provided at a surface of the third inorganic particle (B),

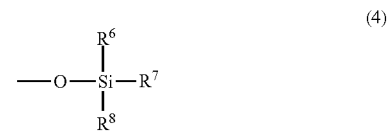

where each of "$R^6$", "$R^7$" and "$R^8$" is, independently, a methyl group or an ethyl group", and
wherein the mass ratio of the third inorganic particle (B) with respect to the gross mass of the first inorganic particle (A1), the second inorganic particle (A2) and the third inorganic particle (B) is greater than or equal to 0.001 and less than or equal to 0.05.

DETAILED DESCRIPTION OF EMBODIMENTS

The invention will be described herein with reference to illustrative embodiments. Those skilled in the art will recognize that many alternative embodiments can be accomplished using the teachings of the present invention and that the invention is not limited to the embodiments illustrated for explanatory purposes.

A dental adhesive agent includes a polymerizable monomer, a first inorganic particle (A1), a second inorganic particle (A2) and a third inorganic particle (B).

The first inorganic particle (A1) and the second inorganic particle (A2) have been subjected to surface treatments with a chemical compound expressed by the general formula (1) and a chemical compound expressed by the general formula (2), respectively. Thus, the bending strength of the dental adhesive agent post-curing can be improved.

The volume median diameter of the first inorganic particle (A1) may be 0.1 to 0.5 μm, and preferably, 0.2 to 0.4 μm. When the volume median diameter of the first inorganic particle (A1) is less than 0.1 μm, the bending strength of the dental adhesive agent post-curing is reduced and the dental adhesive agent is difficult to extrude. When the volume median diameter of the first inorganic particle (A1) exceeds 0.5 μm, the dental adhesive agent becomes thick after being cured.

The volume median diameter of the second inorganic particle (A2) may be 0.6 to 0.9 μm, and preferably, 0.7 to 0.9 μm. When the volume median diameter of the second inorganic particle (A2) is less than 0.6 μm, the dental adhesive agent is difficult to extrude. When the volume median diameter of the second inorganic particle (A2) exceeds 0.9 μm, a cured film of the dental adhesive agent becomes thick.

The volume median diameter of each of the inorganic particles (A1) and (A2) may be measured by a laser diffraction scattering method.

A group expressed by a general formula (3) and/or a group expressed by a general formula (4) exists at a surface of the third inorganic particle (B). With this configuration, the bending strength of the dental adhesive agent post-curing can be improved.

The mean primary-particle diameter of the third inorganic particle (B), at the surface of which the group expressed by the general formula (3) or the group expressed by the general formula (4) exists, may be 5 to 50 nm, and preferably, 5 to 20 nm. When the mean primary-particle diameter of the third inorganic particle (B) is less than 5 nm, it is hard to manufacture the third inorganic particle (B). When the mean primary-particle diameter of the third inorganic particle (B) exceeds 50 nm, the bending strength of the dental adhesive agent post-curing is reduced.

The mean primary-particle diameter of the third inorganic particle (B) here is an average value of 100 primary particles of the third inorganic particle (B) randomly selected from an electron micrograph of the third inorganic particle (B).

The mass ratio of the third inorganic particle (B) with respect to the gross mass of the first inorganic particle (A1), the second inorganic particle (A2) and the third inorganic particle (B) may be 0.001 to 0.05, preferably, 0.001 to 0.019, and more preferably 0.001 to 0.015. When the mass ratio of the third inorganic particle (B) with respect to the gross mass of the first inorganic particle (A1), the second inorganic particle (A2) and the third inorganic particle (B) is less than 0.001, the bending strength of the dental adhesive agent post-curing is reduced. When the mass ratio of the third inorganic particle (B) with respect to the gross mass of the first inorganic particle (A1), the second inorganic particle (A2) and the third inorganic particle (B) exceeds 0.05, the dental adhesive agent is difficult to extrude and the cured film of the dental adhesive agent becomes thick.

The mass ratio of the first inorganic particle (A1) with respect to the second inorganic particle (A2) may be preferably 0.25 to 4, and more preferably, 1 to 3. When the mass ratio of the first inorganic particle (A1) with respect to that of the second inorganic particle (A2) is greater than or equal to 0.25 and less than or equal to 4, filling factor of the first inorganic particle (A1) and the second inorganic particle (A2) is improved, and as a result, the bending strength of the dental adhesive agent post-curing can be improved.

The polymerizable monomer, the first inorganic particle (A1), the second inorganic particle (A2) and the third inorganic particle (B) are described.

The refraction index of a polymer of the polymerizable monomer may be, generally, 1.52 to 1.58, and preferably, 1.53 to 1.58.

The refraction index here means a refraction index measured by an Abbe refractometer at 25° C.

It is preferable that the polymerizable monomer is a radical polymerizable monomer.

As the polymerizable monomer, although not particularly limited, esters such as α-cyanoacrylic acid, (meth)acrylic acid, α-haloacrylic acid, crotonic acid, cinnamic acid, sorbic acid, maleic acid and itaconic acid, (meth)acrylamide, (meth) acrylamide derivative, (meth)acrylate including a urethane bond, vinylester, vinylether, mono-N-vinyl derivative, styrene derivative and the like may be exemplified, and two or more may be used in combination. Among them, the (meth)acrylic ester and the (meth)acrylamide derivative are preferably used, and the (meth)acrylic ester is more preferably used.

As monofunctional (meth)acrylic ester and (meth)acrylamide derivative, methyl(meth)acrylate, isobutyl(meth)acrylate, benzyl(meth)acrylate, lauryl(meth)acrylate, 2,3-dibromopropyl(meth)acrylate, 2-hydroxyethyl(meth)acrylate, 6-hydroxyhexyl (meth)acrylate, 10-hydroxydecyl(meth)acrylate, propylene glycol mono(meth)acrylate, glycerin mono(meth)acrylate, erythritol mono(meth)acrylate, N-methylol(meth)acrylamide, N-hydroxyethyl(meth)acrylamide, N-(dihydroxyethyl)(meth)acrylamide, (meth)acryloyloxydodecylpyridinium bromide, (meth)acryloyloxydodecylpyridinium chloride, (meth)acryloyloxyhexadecylpyridinium chloride, (meth)acryloyloxydecylammonium chloride and the like may be exemplified.

As bifunctional (meth)acrylic ester, ethylene glycol di(meth)acrylate, triethylene glycol di(meth)acrylate, propylene glycol di(meth)acrylate, neopentyl glycol di(meth)acrylate, glycerin di(meth)acrylate, 1,6-hexanediol di(meth)acrylate, 1,10-decanediol di(meth)acrylate, 2,2-bis(4-(3-(meth)acryloyloxy-2-hydroxypropoxy)phenyl)propane, 2,2-bis(4-(2-(meth)acryloyloxyethoxy)phenyl)propane, 2,2-bis(4-(meth)acryloyloxypolyethoxyphenyl)propane, 1,2-bis(3-(meth)acryloyloxy-2-hydroxypropoxy)ethane,
pentaerythritol di(meth)acrylate, (2,2,4-trimethylhexamethylenebis(2-carbamoyloxyethyl)) di(meth)acrylate and the like may be exemplified.

As the (meth)acrylic ester including three or more functional groups, trimethylolpropane tri(meth)acrylate, trimethylolethane tri(meth)acrylate, tetramethylolmethane tri (meth)acrylate, pentaerythritol tetra(meth)acrylate, dipentaerythritol hexa(meth)acrylate, N,N'-(2,2,4-trimethylhexamethylene)bis(2-(aminocarboxy)propane-1,3-diol) tetramethacrylate, 1,7-diacryloyloxy-2,2,6,6-tetraacryloyloxymethyl-4-oxyheptane and the like may be exemplified.

As the (meth)acrylate including the urethane bond, di-2-(meth)acryloxyethyl-2,2,4-trimethylhexamethylenedicarbamate, 1,3,5-tris(1,3-bis((meth)acryloyloxy)-2-propoxycarbonylaminohexane)-1,3,5-(1H,3H,5H)triazine-2,4,6-trione, 2,2-bis(4-(3-(meth)acryloyloxy-2-hydroxypropyl)phenyl)propane, 2,2-bis(4-((meth)acryloxyethoxy)phenyl)propane and the like may be exemplified.

As the (meth)acrylate including the urethane bond other than the above described compounds, a reaction product of 2,2'-di(4-hydroxycyclohexyl)propane, 2-oxepanone, hexamethylene diisocyanate and 2-hydroxyethyl(meth)acrylate, a reaction product of 1,3-butanediol, hexamethylene diisocyanate and 2-hydroxyethyl(meth)acrylate and the like may be exemplified.

The mass ratio of the polymerizable monomer with respect to the gross mass of the first inorganic particle (A1), the second inorganic particle (A2) and the third inorganic particle (B) may be, generally, 0.2 to 0.4, and preferably, 0.25 to 0.35.

The first inorganic particle (A1) may be spherical, but preferably, the first inorganic particle (A1) has an irregular shape. With this, specific surface area of the first inorganic particle (A1) is increased, and bonding with the polymerizable monomer becomes strong so that the bending strength of the dental adhesive agent post-curing can be improved.

As the "$R^2$" of the general formula (1), although not particularly limited, an alkoxy group such as a methoxy group, an ethoxy group and a butoxy group, a chlorine atom, an isocyanate group and the like may be exemplified.

As the "$R^3$" of the general formula" (1), although not particularly limited, an alkyl group whose carbon number is 1 to 6, an alkenyl group whose carbon number is 2 to 6, an alkynyl group whose carbon number is 2 to 6 and the like may be exemplified.

As the alkyl group whose carbon number is 1 to 6, either of a straight-chain type, a branched-chain type and a cyclic type may be used, and a methyl group, an ethyl group, an n-propyl group, an isopropyl group, an n-butyl group, an isobutyl group, a sec-butyl group, a tert-butyl group, an n-pentyl group, an isopentyl group, a neopentyl group, a tert-pentyl group, an n-hexyl group, a cyclopropyl group, a cyclobutyl group, a cyclopentyl group, a cyclohexyl group and the like may be exemplified.

As the alkenyl group whose carbon number is 2 to 6, either of a straight-chain type, a branched-chain type and a cyclic type may be used, and a vinyl group, an allyl group, a methylvinyl group, a butenyl group, a pentenyl group, a hexenyl group, a cyclopropenyl group, a cyclobutenyl group, a cyclopentenyl group, a cyclohexenyl group and the like may be exemplified.

As the alkynyl group whose carbon number is 2 to 6, either of a straight-chain type, a branched-chain type and a cyclic type may be used, and an ethynyl group, a 1-propynyl group, a 2-propynyl group, a 1-butynyl group, a 1-methyl-2-propynyl group, a 2-butynyl group, a 3-butynyl group, a 1-pentynyl group, a 1-ethyl-2-propynyl group, a 2-pentynyl group, a 3-pentynyl group, a 1-methyl-2-butynyl group, a 4-pentynyl group, a 1-methyl-3-butynyl group, a 2-methyl-3-butynyl group, 1-hexynyl group, a 2-hexynyl group, a 1-ethyl-2-butynyl group, a 3-hexynyl group, a 1-methyl-2-pentynyl group, a 1-methyl-3-pentynyl group, a 4-methyl-1-pentynyl group, a 3-methyl-1-pentynyl group, a 5-hexynyl group, a 1-ethyl-3-butynyl group and the like may be exemplified.

The "q" in the general formula (1) is an integer greater than or equal to 6 and less than or equal to 13, and preferably, an integer greater than or equal to 8 and less than or equal to 13.

As the chemical compound expressed by the general formula (1), although not particularly limited, 6-methacryloyloxyhexyltrimethoxysilane, 7-methacryloyloxyheptyltrimethoxysilane, 8-methacryloyloxyoctyltrimethoxysilane, 8-acryloyloxyoctyltrimethoxysilane, 8-methacryloyloxyoctyltriethoxysilane, 9-methacryloyloxynonyltrimethoxysilane, 10-methacryloyloxydecyltrimethoxysilane, 11-methacryloyloxyundecyltrimethoxysilane, 11-methacryloyloxyundecyldichloromethylsilane, 11-methacryloyloxyundecyltrichlorosilane, 11-methacryloyloxyundecyldimethoxymethylsilane, 12-methacryloyloxydodecyltrimethoxysilane, a 13-methacryloyloxytridecyltrimethoxysilane and the like may be exemplified, and two or more may be used in combination. Among them, the 8-methacryloyloxyoctyltrimethoxysilane, the 9-methacryloyloxynonyltrimethoxysilane, the 10-methacryloyloxydecyltrimethoxysilane and the 11-methacryloyloxyundecyltrimethoxysilane are preferably used.

Methods of performing the surface treatment to form the first inorganic particle (A1), although not particularly limited, may include spraying a solution of the chemical compound expressed by the general formula (1) diluted with a solvent on an inorganic particle (A1') while stirring the inorganic particle (A1') in a mixing tank, and heating and drying the inorganic particle (A1') in the tank for a certain period while continuously stirring the inorganic particle (A1'), or stirring and mixing the inorganic particle (A1') and the chemical compound expressed by the general formula (1) in a solvent and then heating and drying the mixture.

The mass ratio of the chemical compound expressed by the general formula (1) with respect to the inorganic particle (A1') before performing the surface treatment may be, generally, 0.005 to 0.15, and preferably, 0.01 to 0.13.

The refraction index of the first inorganic particle (A1) may be, generally, 1.52 to 1.58, and preferably, 1.53 to 1.58.

A difference between the refraction index of the polymer of the polymerizable monomer and the refraction index of the first inorganic particle (A1) may be, generally, less than or equal to 0.03.

As a material composing the inorganic particle (A1') before performing the surface treatment, although not particularly limited, various glasses (an E-glass, a barium glass, a lanthanum glass ceramic, for example) whose main constituent is silica, and including a heavy metal, boron, oxide such as aluminum oxide if necessary, various ceramics, composite oxide (silica-titania composite oxide, silica-zirconia composite oxide, for example), kaoline, clay mineral (montmorillonite, for example), mica, ytterbium fluoride, yttrium fluoride and the like may be exemplified, and two or more may be used in combination.

As a commercial product of the inorganic particle (A1') before performing the surface treatment, G018-053, G018-053, 8235, GM31684 (all manufactured by SCHOTT), E2000, E3000 (all manufactured by Esstech Inc.) and the like may be exemplified.

The second inorganic particle (A2) is the same as the first inorganic particle (A1) except that the volume median diameter of the second inorganic particle (A2) is 0.6 to 0.9 μm.

The third inorganic particle (B) may have a spherical shape or an irregular shape. The third inorganic particle (B) may be a primary particle which is not aggregated, or a secondary particle in which primary particles are aggregated.

When the third inorganic particle (B) has an irregular shape, the primary-particle diameter is an average value of a longitudinal diameter and a shorter diameter of the third inorganic particle (B).

Methods of performing the surface treatment to form the inorganic particles (B), although not particularly limited, may include spraying a solution of a silane coupling agent diluted by a solvent on an inorganic particle (B') while stirring the inorganic particle (B') in a mixing tank, and heating and drying the inorganic particles (B') in the tank for a certain period while continuously stirring the inorganic particle (B'), or stirring and mixing the inorganic particle (B') and the silane coupling agent in a solvent and then heating and drying the mixture.

As the silane coupling agent, although not particularly limited as long as the group expressed by the general formula (3) or the group expressed by the general formula (4) can be introduced at a surface of the third inorganic particle (B), dimethyldichlorosilane, hexamethyldisilazane and the like may be exemplified, and two or more may be used in combination.

As a material composing the inorganic particle (B'), before performing the surface treatment, although not particularly limited, inorganic oxide such as silica, alumina, titania and zirconia, composite oxide, calcium phosphate, hydroxyapatite, yttrium fluoride, ytterbium fluoride, barium titanate, potassium titanate and the like may be exemplified. Among them, the silica, the alumina, the titania, silica-alumina composite oxide, silica-zirconia composite oxide are preferably used.

A commercially available example of the inorganic particle (B') includes AEROSIL 200, OX-50 (all manufactured by NIPPON AEROSIL CO., LTD.) and the like.

A commercially available example of the third inorganic particle (B) includes AEROSIL R812, R972, RX-50 (all manufactured by NIPPON AEROSIL CO., LTD.) and the like.

The refraction index of the third inorganic particle (B) may be, generally, 1.43 to 1.50, and preferably, 1.43 to 1.46.

A difference between the refraction index of the polymer of the polymerizable monomer and the refraction index of the third inorganic particle (B) may be, generally, greater than or equal to 0.05.

The dental adhesive agent may further include a polymerization initiator.

When polymerizing and curing the dental adhesive agent at ambient temperature, a chemical polymerization initiator may be used.

As the chemical polymerization initiator, although not particularly limited, organic peroxide/amine, organic peroxide/amine/sulfinic acid (or sulfinate) and the like may be exemplified.

As an oxidizer, although not particularly limited, an organic peroxide compound such as diacylperoxide, peroxyester, peroxy carbonate, dialkylperoxide, peroxyketal, ketone peroxide and hydroperoxide may be exemplified.

As the diacylperoxide, benzoyl peroxide, 2,4-dichlorobenzoyl peroxide, m-toluoylperoxide, lauroylperoxide and the like may be exemplified.

As the peroxyester, t-butylperoxybenzoate, di-t-butylperoxyisophthalate, t-butylperoxy-2-ethylhexanoate and the like may be exemplified.

As the peroxy carbonate, t-butylperoxyisopropyl carbonate and the like may be exemplified.

As the dialkylperoxide, dicumyl peroxide, di-t-butylperoxide, 2,5-dimethyl-2,5-bis(benzoylperoxy)hexane and the like may be exemplified.

As the peroxyketal, 1,1-bis(t-butylperoxy)-3,3,5-trimethylcyclohexane and the like may be exemplified.

As the ketone peroxide, methylethylketone peroxide and the like may be exemplified.

As the hydroperoxide, t-butylhydro peroxide, cumene hydroperoxide and the like may be exemplified.

As a reducer, although not particularly limited, N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, N,N-dimethyl-3,5-di-t-butylaniline, N,N-bis(2-hydroxyethyl)-p-toluidine, N,N-bis(2-hydroxyethyl)-3,5-dimethylaniline, N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl)-4 t-butylaniline, N,N-bis(2-hydroxyethyl)-3,5-diisopropylaniline, N,N-bis(2-hydroxyethyl)-3,5-di-t-butylaniline, 4-dimethylaminoethyl benzoate, 4-dimethylamino-n-butoxyethyl benzoate, 4-dimethylamino-2-methacryloyloxyethyl benzoate, trimethylamine, triethylamine, N-methyldiethanolamine, N-ethyldiethanolamine, N-n-butyldiethanolamine, N-lauryldiethanolamine, triethanolamine, (2-dimethylamino) ethylmethacrylate, N-methyldiethanolamine dimethacrylate, N-ethyldiethanolamine dimethacrylate, triethanolamine monomethacrylate, triethanolamine dimethacrylate, triethanolamine trimethacrylate and the like may be exemplified.

In addition to the chemical polymerization initiators described above, tributylboron, organic sulfinic acid and the like may be used. In addition, an oxidation-reduction initiator such as cumenehydroperoxide/thiourea, ascorbic acid/$Cu^{2+}$-salt and organic sulfinic acid (or its salt)/amine/inorganic peroxide are also suitable.

When polymerizing and curing the dental adhesive agent by irradiating the dental adhesive with visible light, a photo polymerization initiator may be used.

As the photo polymerization initiator, although not particularly limited, an oxidation-reduction initiator such as α-diketone/reducer, ketal/reducer and thiaxanthon/reducer may be exemplified.

As the α-diketone, camphorquinone, benzyl, 2,3-pentanedione and the like may be exemplified.

As the ketal, benzyldimethylketal, benzyldiethylketal and the like may be exemplified.

As the thiaxanthon, 2-chlorothiaxanthon, 2,4-diethylthiaxanthon and the like may be exemplified.

As the reducer, tertiary amine such as Michler's ketone, 2-(dimethylamino)ethylmethacrylate, N,N-bis((meth)acryloyloxyethyl)-N-methylamine, N,N-dimethylaminoethyl benzoate, 4-dimethylaminobutyl benzoate, 4-dimethylaminobutoxyethyl benzoate, N-methyldiethanolamine, 4-dimethylaminobenzophenone, N,N-bis(2-hydroxyethyl)-p-toluidine and dimethylamino phenanthol; aldehyde such as citronellal, laurylaldehyde, phthaldialdehyde, dimethylaminobenzaldehyde and terephthalaldehyde; a chemical compound including a thiol group such as 2-mercaptobenzoxazole, decanethiol, 3-mercaptopropyltrimethoxysilane, 4-mercaptoacetophenone, 2-mercaptobenzoic acid and thiobenzoic acid, and the like may be exemplified.

When the oxidation-reduction initiator is used as the photo polymerization initiator, organic peroxide may be used together.

When polymerizing and curing the dental adhesive agent by irradiating the dental adhesive agent with ultraviolet light, a photo polymerization initiator may be used.

As the photo polymerization initiator in such a case, although not particularly limited, benzoinalkylether, benzyldimethylketal, acylphosphine oxide, bisacylphosphine oxide and the like may be exemplified.

As the acylphosphine oxide, 2,4,6-trimethylbenzoyldiphenylphosphine oxide, 2,6-dimethoxy benzoyldiphenylphosphine oxide, 2,6-dichlorobenzoyldiphenylphosphine oxide, 2,3,5,6-tetramethylbenzoyldiphenylphosphine oxide, benzoylbis(2,6-dimethylphenyl) phosphonate, 2,4,6-trimethylbenzoylethoxyphenylphosphine oxide and the like may be exemplified.

As the bisacylphosphine oxide, bis(2,6-dichlorobenzoyl) phenylphosphine oxide, bis(2,6-dichlorobenzoyl)-2,5-dimethylphenylphosphine oxide, bis(2,6-dichlorobenzoyl)-4-propylphenylphosphine oxide, bis(2,6-dichlorobenzoyl)-1-naphthylphosphine oxide, bis(2,6-dimethoxy benzoyl) phenylphosphine oxide, bis(2,6-dimethoxy benzoyl)-2,4,4-trimethylpentylphosphine oxide, bis(2,6-dimethoxy benzoyl)-2,5-dimethylphenylphosphine oxide, bis(2,4,6-trimethylbenzoyl)phenylphosphine oxide and the like may be exemplified.

The (bis)acylphosphine oxide may be substituted by a water-soluble substituent group.

The (bis)acylphosphine oxide may be used with a reducer such as amine, aldehyde, mercaptan, and sulfinic acid salt.

The mass ratio of the polymerization initiator with respect to the polymerizable monomer may be, generally, 0.001 to 0.1, and preferably, 0.002 to 0.05.

The dental adhesive agent may further include a polymerization inhibitor, an ultraviolet absorber, a fluorescent, a pigment and the like.

As the polymerization inhibitor, although not particularly limited, 3,5-dibutyl-4-hydroxytoluene, hydroquinone, dibutylhydroquinone, dibutylhydroquinone monomethylether, 2,6-t-butylphenol, 4-methoxy phenol, 6-tert-butyl-2,4-xylenol and the like may be exemplified, and two or more may be used in combination.

The dental adhesive agent includes a paste in which the first inorganic particle (A1), the second inorganic particle (A2) and the third inorganic particle (B) are dispersed in the polymerizable monomer, for example.

When the chemical polymerization initiator (and the photo polymerization initiator) is used, the dental adhesive agent is configured as a two-part adhesive agent (2 pastes) in which a first composition (paste) including the oxidizer which constitutes the chemical polymerization initiator, and a second composition (paste) in which the reducer which constitutes the chemical polymerization initiator are separately packed. In such a case, it is necessary to mix the first composition and the second composition right before using the dental adhesive agent to polymerize and cure. Here, compositions of the inorganic particles included in the first composition and the second composition, respectively, may be the same or different.

When the photo polymerization initiator is used, the dental adhesive agent is configured as a one-part adhesive agent (1 paste) of a composition including the photo polymerization initiator.

The dental adhesive agent may be provided as a package including a syringe in which the dental adhesive agent is filled, a plunger that is fitted in the syringe from a back end side of the syringe, and a needle tip that is to be attached to a front end portion of the syringe, for example.

An inner diameter of a needle of the needle tip may be, generally, 0.3 to 0.9 mm.

When the dental adhesive agent is configured as the two-part adhesive agent (2 pastes), the package may include two syringes that are connected in parallel, two plungers that are connected in parallel, and a static mixer provided at front end portions of the syringes, for example.

EXAMPLES

The present embodiment is described with reference to examples and comparative examples. However, the present embodiment is not limited to the examples. In the following, "part" means "mass part" or "mass %".

(Preparation of Inorganic Particle (A1-1))

By performing a surface treatment on irregular shaped barium glass particles G018-053 NanoFine180 (manufactured by SCHOTT), whose volume median diameter was 0.18 µm, by 8-methacryloyloxyoctyltrimethoxysilane, inorganic particles (A1-1), whose volume median diameter was 0.18 µm, were obtained.

(Preparation of Inorganic Particle (A1-2))

By performing a surface treatment on barium glass particles G018-053 Ultra Fine0.4 (manufactured by SCHOTT), whose volume median diameter was 0.4 µm, by 8-methacryloyloxyoctyltrimethoxysilane, inorganic particles (A1-2), whose volume median diameter was 0.4 µm, were obtained.

(Preparation of Inorganic Particle (A1-3))

By performing a surface treatment on barium glass particles G018-053 Ultra Fine0.4 (manufactured by SCHOTT), whose volume median diameter was 0.4 µm, by 3-methacryloyloxypropyltrimethoxysilane, inorganic particles (A1-3), whose volume median diameter was 0.4 µm, were obtained.

(Preparation of Inorganic Particle (A2-1))

By performing a surface treatment on barium glass particles G018-053 Ultra Fine0.7 (manufactured by SCHOTT), whose volume median diameter was 0.7 µm, by 8-methacryloyloxyoctyltrimethoxysilane, inorganic particles (A2-1), whose volume median diameter was 0.7 µm, were obtained.

(Preparation of Inorganic Particle (A2-2))

By performing a surface treatment on strontium glass particles, whose volume median diameter was 0.8 µm, by 8-methacryloyloxyoctyltrimethoxysilane, inorganic particles (A2-2), whose volume median diameter was 0.8 µm, were obtained.

(Preparation of Inorganic Particle (A2-3))

By performing a surface treatment on barium glass particles G018-053 Ultra Fine0.7 (manufactured by SCHOTT), whose volume median diameter was 0.7 µm, by 3-methacryloyloxypropyltrimethoxysilane, inorganic particles (A2-3), whose volume median diameter was 0.7 µm, were obtained.

Table 1 illustrates characteristics of the inorganic particles (A1) and (A2).

[Table 1]

TABLE 1

| INORGANIC PARTICLE | MATERIAL | VOLUME MEDIAN DIAMETER [μm] | SURFACE TREATMENT AGENT |
|---|---|---|---|
| A1-1 | BARIUM GLASS | 0.18 | 8-methacryloyloxyoctyltrimethoxysilane |
| A1-2 | BARIUM GLASS | 0.40 | 8-methacryloyloxyoctyltrimethoxysilane |
| A1-3 | BARIUM GLASS | 0.40 | 3-methacryloyloxypropyltrimethoxysilane |
| A2-1 | BARIUM GLASS | 0.70 | 8-methacryloyloxyoctyltrimethoxysilane |
| A2-2 | STRONTIUM GLASS | 0.80 | 8-methacryloyloxyoctyltrimethoxysilane |
| A2-3 | BARIUM GLASS | 0.70 | 3-methacryloyloxypropyltrimethoxysilane |

(Volume Median Diameter of Inorganic Particles (A1) and (A2))

After adding 15 mg of the inorganic particles (A1) or (A2) to 20 mL of 0.2 mass % sodium hexametaphosphate solution, the solution was dispersed by using an ultrasonic dispersion device for 30 minutes to obtain dispersion of the inorganic particles (A1) or (A2). Next, the volume median diameter of the inorganic particles (A1) or (A2) was measured by using a particle size distribution analyzer using laser beams LA-950 (manufactured by HORIBA, Ltd.).

(Inorganic Particle (B-1))

Silica particles AEROSIL (registered trademark) RX50 (manufactured by NIPPON AEROSIL CO., LTD.), on which a surface treatment by hexamethyldisilazane was performed and whose mean primary-particle diameter was 40 nm, were used as inorganic particles (B-1).

(Inorganic Particle (B-2))

Silica particles AEROSIL (registered trademark) R972 (manufactured by NIPPON AEROSIL CO., LTD.), on which a surface treatment by dimethyldichlorosilane was performed and whose mean primary-particle diameter was 16 nm, were used as inorganic particles (B-2).

(Inorganic Particle (B-3))

Silica particles AEROSIL (registered trademark) R812 (manufactured by NIPPON AEROSIL CO., LTD.), on which a surface treatment by hexamethyldisilazane was performed and whose mean primary-particle diameter was 7 nm, were used as inorganic particles (B-3).

(Preparation of Inorganic Particle (B-4))

By performing a surface treatment on silica particles AEROSIL (registered trademark) 200 (manufactured by NIPPON AEROSIL CO., LTD.), whose mean primary-particle diameter was 12 nm, by 3-methacryloyloxypropyltrimethoxysilane, inorganic particles (B-4), whose mean primary-particle diameter was 12 nm, were obtained.

Table 2 illustrates characteristics of the inorganic particles (B).

TABLE 2

| INORGANIC PARTICLE | MATERIAL | MEAN PRIMARY-PARTICLE DIAMETER [nm] | SURFACE TREATMENT AGENT |
|---|---|---|---|
| B-1 | SILICA | 40 | hexamethyldisilazane |
| B-2 | SILICA | 16 | dimethyldichlorosilane |
| B-3 | SILICA | 7 | hexamethyldisilazane |
| B-4 | SILICA | 12 | 3-methacryloyloxypropyltrimethoxysilane |

(Mean Primary-Particle Diameter of Third Inorganic Particle (B))

After performing an image analysis on an electron micrograph of 100 inorganic particles (B) by using image analysis software WinROOF (manufactured by MITANI CORPORATION), the mean primary-particle diameter of the inorganic particles (B) was calculated as a volume mean diameter.

(Preparation of Polymerizable Monomer Composition A)

By mixing 60 parts of di-2-methacryloyloxyethyl-2,2,4-trimethylhexamethylenedicarbamate, 10 parts of bisphenol A diglycidyl methacrylate, 20 parts of glycerin dimethacrylate and 10 parts of neopentyl glycol dimethacrylate, a polymerizable monomer mixture A was obtained.

By adding 0.4 parts of camphorquinone, 2 parts of 4-dimethylaminoethyl benzoate, 2 parts of N,N-bis(2-hydroxyethyl)-p-toluidine and 0.05 parts of 6-tert-butyl-2,4-xylenol to the polymerizable monomer mixture A, a polymerizable monomer composition A was obtained.

(Preparation of Polymerizable Monomer Composition B)

By mixing 70 parts of di-2-methacryloyloxyethyl-2,2,4-trimethylhexamethylenedicarbamate, 20 parts of glycerin dimethacrylate and 10 parts of neopentyl glycol dimethacrylate, a polymerizable monomer mixture B was obtained.

By adding 2.6 parts of benzoyl peroxide, 1.8 parts of cumene hydroperoxide and 0.22 parts of 3,5-dibutyl-4-hydroxytoluene to the polymerizable monomer mixture B, a polymerizable monomer composition B was obtained.

Examples 1 to 8 and Comparative Examples 1 to 6

100 parts of the inorganic particles whose composition (parts) was as illustrated in Table 3 were added to 30 parts of the polymerizable monomer composition A, the mixture was mixed and kneaded until uniform, and thereafter, degassed under vacuum to obtain a paste 1, for each of examples 1 to 8 and comparative examples 1 to 6.

100 parts of the inorganic particles having the composition (parts) as indicated in Table 3 were added to 30 parts of the polymerizable monomer composition B, the mixture was mixed and kneaded to be uniform, and thereafter, degassed under vacuum to obtain a paste 2, for each of examples 1 to 8 and comparative examples 1 to 6.

As described above, a two-part adhesive agent composed of the paste 1 and the paste 2 was prepared, for each of examples 1 to 8 and comparative examples 1 to 6.

TABLE 3

| | | EXAMPLE | | | | | | | | COMPARATIVE EXAMPLE | | | | | |
|---|---|---|---|---|---|---|---|---|---|---|---|---|---|---|---|
| | | 1 | 2 | 3 | 4 | 5 | 6 | 7 | 8 | 1 | 2 | 3 | 4 | 5 | 6 |
| INORGANIC PARTICLE | A1-1 | | 69.5 | | | 59.3 | 20 | | | | | | | | 69 |
| | A1-2 | 70.3 | | 49 | 29.6 | | 20 | 39.9 | 70.3 | | | | 70.8 | 25 | |
| | A1-3 | | | | | | | | | | | 70.8 | | | |
| | A2-1 | 28.9 | 29.7 | 49 | 69.3 | | 30 | | 28.1 | 49 | | | 28.4 | 65 | 29.5 |
| | A2-2 | | | | | 39.5 | 30 | 59 | | 49 | 99.2 | | | | |
| | A2-3 | | | | | | | | | | | | | 28.4 | |
| | B-1 | | | 1.5 | 0.3 | 0.2 | | | 1.6 | 1.5 | 0.8 | | | | |
| | B-2 | 0.5 | 0.5 | 0.5 | 0.3 | | | 0.6 | | 0.5 | | 0.8 | 0.8 | | |
| | B-3 | 0.3 | 0.3 | | 0.5 | 1 | 1 | 0.5 | | | | | | 10 | |
| | B-4 | | | | | | | | | | | | | | 1.5 |
| TOTAL | | 100 | 100 | 100 | 100 | 100 | 100 | 100 | 100 | 100 | 100 | 100 | 100 | 100 | 100 |

Next, the extrusion strength of the adhesive agent, the post-curing bending strength and the thickness of a cured film were evaluated, for each of examples 1 to 8 and comparative examples 1 to 6.

(Post-Curing Bending Strength)

After filling the adhesive agent in a mold base, made of stainless steel with dimensions of 2 mm×2 mm×25 mm, using a two paste mixing syringe made of polypropylene-based resin, to which a mixing tip can be attached, the mold base was pressed from upper and lower sides by slide glasses, respectively. Next, the adhesive agent was cured by irradiating visible light from the upper and lower sides, at 9 points for each side with 10 seconds for each point, using a G-Light Prima II (manufactured by GC). After detaching a cured product from the mold base, the cured product was kept in distilled water at 37° C. for 24 hours to obtain a test piece. 5 test pieces were prepared for each example.

Next, the bending strength of each of the 5 test pieces was measured by using a universal test device AG-IS (manufactured by Shimadzu Corporation) while setting a distance of 20 mm between the supporting points, and a speed of 1 mm/min for a cross-head. Then, an average value of the bending strengths of the 5 test pieces was calculated. Here, it was determined to be acceptable when the average value of the bending strengths of the test pieces was greater than or equal to 180 MPa.

(Extrusion Strength)

Extrusion strength of the adhesive agent was measured by using a two paste mixing syringe made of polypropylene-based resin, to which a mixing tip can be attached.

First, 4.0 mL of the paste 1 and 4.0 mL of the paste 2 were filled in the syringe, respectively, and the mixing tip was attached to a front end of the syringe. Then, by pushing a plunger, a mixed adhesive agent was extruded from a front end of the tip.

Extrusion strength of the adhesive agent was measured by a universal test device AG-IS (manufactured by Shimadzu Corporation) at 25° C. Specifically, while retaining a storage container in a vertical direction, the adhesive agent was extruded while applying a load to the adhesive agent by lowering a cross-head to which a jig for testing compressive strength was attached at 10 mm/min, and the maximum load was used as the extrusion strength. Here, it was determined to be acceptable when the extrusion strength was less than or equal to 5 kgf.

(Thickness of Cured Film)

The thickness of the cured film of the adhesive agent was evaluated using two optically flat foursquare glass plates each having a contacting surface area of approximately 200 mm$^2$ with a thickness greater than or equal to 5 mm.

The two glass plates were overlapped such that their contacting surfaces were facing with each other, and a thickness "A" was measured by using a micrometer at accuracy greater than or equal to 1 μm.

0.02 to 0.1 mL of the adhesive agent was placed on a contacting surface of one of the glass plates by using a two paste mixing syringe made of polypropylene-based resin at which a mixing tip can be attached. Then, the glass plate was placed on a platen of a load device. Then, the other of the glass plates was placed on the one of the glass plates on which the adhesive agent was placed such that their contacting surfaces were facing with each other. Immediately thereafter, vertical force of 150±2N was applied to a center of the adhesive agent via the glass plates for 180±10 seconds. At this time, the adhesive agent was placed to completely fill a space between the two glass plates. After releasing the vertical force, visible light was irradiated through a center of the contacting surfaces of the glass plates by using a G-LIGHT PRIMA II (manufactured by GC) for 40 seconds. The two glass plates that were bonded by the adhesive agent were detached from the load device. Then, a thickness "B" was measured by using a micrometer at accuracy greater than or equal to 1 μm. Then, the thickness of the cured film of the adhesive agent was obtained from a formula "B-A".

The thicknesses of the 5 cured films of the adhesive agent were obtained for each example by the above described procedures, and an average value of them was calculated. Here, it was determined to be acceptable when the average value of the thicknesses of the cured films of the adhesive agent was less than or equal to 15 μm.

Table 4 illustrates evaluated results of the extrusion strength of the adhesive agent, the post-curing bending strength and the thickness of the cured film.

TABLE 4

| | POST-CURING BENDING STRENGTH [MPa] | EXTRUSION STRENGTH [kgf] | THICKNESS OF CURED FILM [μm] |
|---|---|---|---|
| EXAMPLE 1 | 194 | 3 | 10 |
| EXAMPLE 2 | 186 | 4 | 11 |
| EXAMPLE 3 | 182 | 2 | 13 |
| EXAMPLE 4 | 192 | 3 | 15 |
| EXAMPLE 5 | 188 | 3 | 13 |
| EXAMPLE 6 | 194 | 2 | 14 |
| EXAMPLE 7 | 187 | 2 | 13 |
| EXAMPLE 8 | 185 | 4 | 14 |
| COMPARATIVE EXAMPLE 1 | 204 | 7 | 17 |

TABLE 4-continued

| | POST-CURING BENDING STRENGTH [MPa] | EXTRUSION STRENGTH [kgf] | THICKNESS OF CURED FILM [μm] |
|---|---|---|---|
| COMPARATIVE EXAMPLE 2 | 182 | 7 | 18 |
| COMPARATIVE EXAMPLE 3 | 188 | 9 | 30 |
| COMPARATIVE EXAMPLE 4 | 190 | 8 | 25 |
| COMPARATIVE EXAMPLE 5 | 177 | 8 | 19 |
| COMPARATIVE EXAMPLE 6 | 175 | 5 | 11 |

From the results of Table 4, it can be understood that the post-curing bending strength is high and the extrusion strength and the thickness of the cured film are low, respectively, for the adhesive agent of each of the examples 1 to 8.

On the other hand, as the adhesive agent of each of the comparative examples 1 and 2 does not include the first inorganic particle (A1), the extrusion strength and the thickness of the cured film were increased, respectively.

As the adhesive agent of the comparative example 3 includes the inorganic particle (A1-3) on which the surface treatment by 3-methacryloyloxypropyltrimethoxysilane, which was inconsistent with the general formula (1), was performed, the extrusion strength and the thickness of the cured film were increased, respectively.

As the adhesive agent of the comparative example 4 includes the inorganic particle (A2-3) on which the surface treatment by 3-methacryloyloxypropyltrimethoxysilane, which was inconsistent with the general formula (2), was performed, the extrusion strength and the thickness of the cured film were increased, respectively.

For the adhesive agent of the comparative example 5, because the mass ratio of the inorganic particle (B-3) with respect to the gross mass of the inorganic particle (A1-2), the inorganic particle (A2-1) and the inorganic particle (B-3) is 0.1, the post-curing bending strength was reduced, and the extrusion strength and the thickness of the cured film were increased, respectively.

As the adhesive agent of the comparative example 6 includes the inorganic particle (B-4) on which the surface treatment by 3-methacryloyloxypropylt rimethoxysilane was performed, and the group expressed by the general formula (3) or (4) was not present at a surface of the inorganic particle (B-4), the post-curing bending strength was reduced.

According to the embodiment, a dental adhesive agent whose post-curing bending strength is high and capable of being easily extruded can be provided.

Although a preferred embodiment of the dental adhesive agent and the method of manufacturing the dental adhesive agent has been specifically illustrated and described, it is to be understood that modifications may be made therein without departing from the spirit and scope of the invention as defined by the claims.

The present invention is not limited to the specifically disclosed embodiments, and numerous variations and modifications may be made without departing from the spirit and scope of the present invention.

What is claimed is:
1. A dental adhesive agent, comprising:
a polymerizable monomer;
a first inorganic particle (A1) that has been subjected to a surface treatment with a chemical compound expressed by a general formula (1),

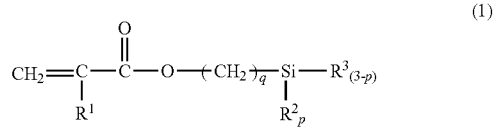

(1)

where "$R^1$" is a hydrogen atom or a methyl group, "$R^2$" is a hydrolyzable group, "$R^3$" is a hydrocarbon group whose carbon number is greater than or equal to 1 and less than or equal to 6, "p" is 2 or 3 and "q" is an integer greater than or equal to 6 and less than or equal to 13, the first inorganic particle (A1) having a volume median diameter greater than or equal to 0.1 μm and less than or equal to 0.5 μm;
a second inorganic particle (A2) that has been subjected to a surface treatment with a chemical compound expressed by a general formula (2),

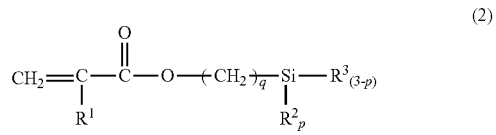

(2)

where "$R^1$" is a hydrogen atom or a methyl group, "$R^2$" is a hydrolyzable group, "$R^3$" is a hydrocarbon group whose carbon number is greater than or equal to 1 and less than or equal to 6, "p" is 2 or 3 and "q" is an integer greater than or equal to 6 and less than or equal to 13, the second inorganic particle (A2) having a volume median diameter greater than or equal to 0.6 μm and less than or equal to 0.9 μm; and
a third inorganic particle (B), having a mean primary-particle diameter greater than or equal to 5 nm and less than or equal to 50 nm, wherein a group expressed by a general formula (3) and/or a group expressed by a general formula (4) is provided at a surface of the third inorganic particle (B),

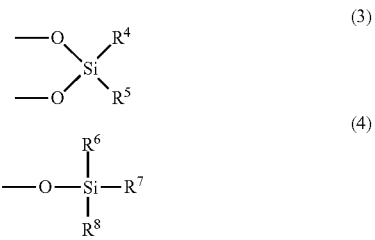

where each of "$R^4$", "$R^5$", "$R^6$", "$R^7$" and "$R^8$" is, independently, a methyl group or an ethyl group",
wherein the mass ratio of the third inorganic particle (B) with respect to the gross mass of the first inorganic particle (A1), the second inorganic particle (A2) and the third inorganic particle (B) is greater than or equal to 0.001 and less than or equal to 0.05, and wherein the mass ratio of the first inorganic particle (A1) with respect to the mass ratio of the second inorganic particle (A2) is greater than or equal to 0.25 and less than or equal to 4.

2. A method of manufacturing the dental adhesive agent of claim 1, comprising:

mixing a composition including at least a part of the polymerizable monomer, the first inorganic particle (A1), the second inorganic particle (A2) and the third inorganic particle (B).

3. The dental adhesive agent according to claim 1, wherein a refraction index of a polymer of the polymerizable monomer is 1.52 to 1.58.

4. The dental adhesive agent according to claim 1, wherein a refraction index of the first inorganic particle (A1) is 1.52 to 1.58.

5. The dental adhesive agent according to claim 1, wherein a difference between a refraction index of a polymer of the polymerizable monomer and a refraction index of the first inorganic particle (A1) is less than or equal to 0.03.

6. The dental adhesive agent according to claim 1, wherein a refraction index of the third inorganic particle (B) is 1.43 to 1.50.

7. The dental adhesive agent according to claim 1, wherein a difference between a refraction index of a polymer of the polymerizable monomer and a refraction index of the third inorganic particle (B) is greater than or equal to 0.05.

8. The dental adhesive agent according to claim 1, wherein the volume median diameter of the first inorganic particle (A1) is 0.2 µm to 0.4 µm.

9. The dental adhesive agent according to claim 1, wherein the volume median diameter of the second inorganic particle (A2) is 0.7 µm to 0.9 µm.

10. The dental adhesive agent according to claim 1, wherein the mass ratio of the third inorganic particle (B) with respect to the gross mass of the first inorganic particle (A1), the second inorganic particle (A2) and the third inorganic particle (B) is greater than or equal to 0.001 and less than or equal to 0.019.

11. The dental adhesive agent according to claim 1, wherein the mass ratio of the chemical compound expressed by the general formula (1) with respect to the first inorganic particle (A1) before performing the surface treatment is greater than or equal to 0.005 and less than or equal to 0.15.

* * * * *